(12) United States Patent
Schwab et al.

(10) Patent No.: US 6,387,934 B1
(45) Date of Patent: May 14, 2002

(54) 2-CYANO-3,5-DIHYDROXYHEX-2-ENECARBOXAMIDE DERIVATIVES

(75) Inventors: Wilfried Schwab, Wiesbaden; Ruth Raiss, Frankfurt, both of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/694,036

(22) Filed: Oct. 23, 2000

Related U.S. Application Data

(62) Division of application No. 09/448,449, filed on Nov. 24, 1999, now Pat. No. 6,172,103, which is a division of application No. 08/927,085, filed on Sep. 10, 1997, now Pat. No. 6,121,316.

(30) Foreign Application Priority Data

Sep. 12, 1996 (DE) .......................... 196 36 974

(51) Int. Cl.[7] ...................... A61K 31/435; A61K 31/44; C07D 211/82; C07D 211/70
(52) U.S. Cl. ...................... 514/358; 514/277; 546/329; 546/330
(58) Field of Search ............... 546/329, 330; 514/277, 358

(56) References Cited

FOREIGN PATENT DOCUMENTS

| EP | 0 652 214 | 5/1995 |
|---|---|---|
| WO | WO 94/24095 | 10/1994 |

OTHER PUBLICATIONS

Nomenclature of Organic Chemistry (P–56, 1979 edition) editors, J. Rigaudy and S.P. Klesney, Pergamon Press.
Derwent Abstract of EP–A–0 652 214.

Sizov et al., "Acylation of Cyanoacetic Ester With Diacid Chlorides Under Phase Transfer Catalysis," Chemical Abstracts, vol. 109, No. 13, Abstract No. 109846a, 1988.

Hart, "Current Concepts in the Rheumatic Diseases: Etiology and Treatment," Seminars in Arthritis and Rheumatism, 15(2)(1):4–7 (1985).

Kang et al., "Scientific Workshop on the Biology and Pathology of Acquired Connective Tissue Diseases," Arthritis and Rheumatism, 35(11):1289–1295 (1992).

Coughlan et al., (CA 123:285095, Abstract of WO 9424095).

D. Burkhardt et al., "Laboratory Evaluation of Glycosaminoglycan Polysulphate Ester for Chondroprotective Activity: A Review", Current Therapeutic Research, 40(6): 1034–1053 (1986).

*Primary Examiner*—Sabiha Qazi
(74) *Attorney, Agent, or Firm*—Finnegan, Henderson, Farabow, Garrett & Dunner, LLP

(57) ABSTRACT

2-Cyano-3,5-dihydroxyhex-2-enecarboxamide derivatives

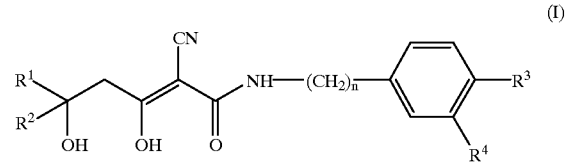

are suitable for the production of pharmaceuticals for the prophylaxis and therapy of diseases or disorders whose course involves increased connective tissue or cartilage degradation.

19 Claims, No Drawings

2-CYANO-3,5-DIHYDROXYHEX-2-ENECARBOXAMIDE DERIVATIVES

This application is a division of Ser. No. 09/448,449 filed Nov. 24, 1999, now U.S. Pat. No. 6,172,103 which is a division of Ser. No. 08/927,085 filed Sep. 10, 1997 now U.S. Pat. No. 6,121,316.

The invention relates to 2-cyano-3,5-dihydroxyhex-2-enecarboxamide derivatives, processes for their preparation and use thereof as pharmaceuticals.

Hyaline articular cartilage is an elastic supportive and lubricant tissue, whose biomechanical function is guaranteed by the special architecture of its matrix and its controlled renewal on the part of the cartilage cells or chondrocytes. Degenerative joint disorders such as arthroses, but also inflammatorily, immunologically or metabolically related arthritides and arthropathies are characterized by a progressive destruction of cartilage, which can lead via functional impairment and pain up to complete ankylosis. Even if different triggers have been held responsible for the various disease forms, according to the general school of thought it is common to the resulting loss of cartilage that it begins with increased proteoglycan degradation and is controlled by the chondrocytes.

For degenerative joint disorders, conventional therapeutics for these disorders are especially nonsteroidal antiinflammatories, and for autoimmunologically pronounced arthritis so-called base therapeutics such as gold compounds, penicillamine, chloroquine derivatives and methotrexate or combinations thereof, but it is common to all of them that they are not able to delay the progressive cartilage destruction.

Arthrosis is a degenerative joint disorder with inflammatory episodes and progressive cartilage destruction which can lead to functional impairment up to complete ankylosis. Until now, the accompanying inflammations and pain conditions in this disorder have been treatable, but there are no pharmaceuticals available which have been shown to be able to delay or to heal the progressive cartilage destruction. Known therapeutics for arthrosis are, for example, mixtures of sulfated glucosaminoglycans (Current Therapeutic Research, 40,6 (1986) 1034) or nonsteroidal antiinflammatories which, however, are not able to delay the cartilage loss.

Even if the pathogenesis of arthrosis is still not clarified in detail, it is regarded as certain that the chondrocytes (cartilage cells) are decisively involved in the increased matrix loss, and that of the main constituents of this matrix, especially the proteoglycans (PG) are the first to be enzymatically degraded.

It has now been found that the compounds of the formula I according to the invention either directly stimulate the proteoglycan synthesis of the cartilage cell or inhibit the increased proteoglycan degradation induced by interleukin-1.

On account of their pharmacological properties, the compounds according to the invention are outstandingly suitable for the treatment and prophylaxis of degenerative joint disorders, but also of disorders of the rheumatic type in which cartilage degradation is to be noted, such as in chronic polyarthritis, joint trauma and in chondrolysis after relatively long immobilization of the joint.

The invention relates to a compound of the formula I

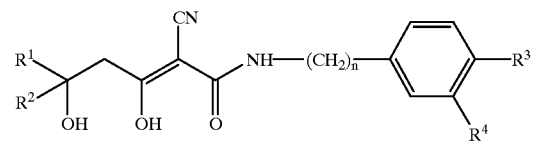

(I)

and/or an optionally stereoisomeric form of the compound of the formula I and/or a physiologically tolerable salt of the compound of the formula I, where $R^1$ is
a) a hydrogen atom or
b) $(C_1-C_4)$-alkyl, $R^2$ is
a) $(C_1-C_{12})$-alkyl,
b) $(C_2-C_{12})$-alkenyl,
C) $(C_2-C_{12})$-alkynyl,
d) $(C_3-C_7)$-cycloalkyl,
e) a 4- to 7-membered heterocyclic radical having 1 or 2 heteroatoms from the group consisting of oxygen, nitrogen and sulfur
f) phenyl,
g) phenyl, mono to trisubstituted by
 1) $(C_1-C_4)$-alkyl,
 2) halogen,
 3) —CN,
 4) —$CF_3$,
 5) —O—$(C_1-C_4)$-alkyl,
 6) —O—$(C_1-C_4)$-alkyl substituted by phenyl, or
 7) methylenedioxyl,
h) $(C_1-C_6)$-alkyl, monosubstituted by
 1) phenyl or
 2) a radical of the formula II

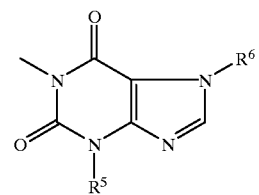

(II)

in which $R^5$ and $R^6$ independently of one another are a hydrogen atom or $(C_1-C_4)$-alkyl,
i) $(C_2-C_6)$-alkenyl, monosubstituted by phenyl or a radical of the formula II, or
k) $(C_2-C_6)$-alkynyl, monosubstituted by phenyl or a radical of the formula II, or
l) $R^1$ and $R^2$ together are=O, $R^3$ is
a) —$CF_3$,
b) —O—$CF_3$,
c) —S—$CF_3$,
d) —OH,
e) —$NO_2$,
f) halogen,
g) benzyl,
h) phenyl,
i) —O-phenyl,
j) a hydrogen atom,
k) —CN, l) —O-phenyl, mono- or polysubstituted by
  1) $(C_1–C_4)$-alkyl,
  2) halogen,
  3) —O—$CF_3$ or
  4) —O—$CH_3$,
$R^4$ is
  a) $(C_1–C_4)$-alkyl,
  b) halogen, or
  c) a hydrogen atom, and
n is the integer zero, 1, 2, 3 or 4.

A compound of the formula I and/or a physiologically tolerable salt of the compound of the formula I and/or an optionally stereoisomeric form of the compound of the formula I is preferred, where
$R^1$ is a hydrogen atom or methyl,
$R^2$ is
  a) $(C_1–C_4)$-alkyl,
  b) $(C_2–C_7)$-alkenyl,
  c) cyclopropyl,
  d) phenyl,
  e) a 5- to 6-membered heterocyclic radical from the group consisting of
    1) pyridine,
    2) furan or
    3) thiophene,
  f) phenyl, mono- to trisubstituted by
    1) methyl,
    2) —CN,
    3) —$CF_3$,
    4) —O-methyl,
    5) —O-methylphenyl or
    6) methylenedioxyl,
  g) $(C_1–C_4)$-alkyl substituted by the radical of the formula II, in which $R^5$ and $R^6$ independently of one another are methyl or propyl,
  h) vinyl, substituted by phenyl, or
  i) ethynyl, substituted by phenyl, or
  k) $R^1$ and $R^2$ together are=0,
$R^3$ is
  a) —$CF_3$,
  b) —Cl or
  c) methyl,
$R^4$ is a hydrogen atom or methyl, and
n is the integer zero, 1 or 2.

A compound of the formula I and/or a physiologically tolerable salt of the compound of the formula I and/or an optionally stereoisomeric form of the compound of the formula I is particularly preferred, where
$R^1$ is a hydrogen atom or methyl,
$R^2$ is a) methyl
  b) butyl,
  c) vinyl,
  d) 1-methylethenyl,
  e) 2-methylpropenyl,
  f) 2,6-dimethylhepta-1,5-dienyl,
  g) cyclopropyl,
  h) phenyl,
  i) phenyl, mono-or polysubstituted by
    1) methylenedioxyl,
    2) 4-methyl,
    3) benzyloxy,
    4) 4-trifluoromethyl,
    5) cyano or
    6) 3,4,5-trimethoxy,
  k) furanyl,
  l) pyridyl,
  m) thiophenyl or
  n) ethynylphenyl, or
  o) $R^1$ and $R^2$ together are=0,
$R^3$ is a) —$CF_3$,
  b) —Cl or
  c) a hydrogen atom,
$R^4$ is a hydrogen atom or methyl and
n is the integer zero, 1 or 2.

The term akyl, alkenyl or alkynyl is understood as meaning radicals whose carbon chain can be straight-chain, branched or cyclic; the double or triple bonds can occur several times. Cyclic alkyl radicals are, for example, 3- to 7-membered monocycles such as cyclopropyl, cyclobutyl, cyclopentyl, cyclohexyl or cycloheptyl. The term "4- to 7-membered heterocyclic radical having 1 or 2 heteroatoms from the group consisting of oxygen, nitrogen and sulfur" includes, for example, radicals which are derived from azetidine, pyrrole, pyran, azepine, pyrroline, pyrrolidine, pyridine, piperidine, imidazole, pyrimidine, furan, 1,2-diazepine, oxazole, pyrazine, piperazine, isoxazole, isoxazoline, morpholine, thiazole, isothiazole, isothiazolidine, thiomorpholine, thiopyran or thiophene. Halogen is chlorine, bromine, iodine or fluorine.

Suitable physiologically tolerable salts of the compound of the formula I are, for example, alkali metal, alkaline earth metal and ammonium salts including those of organic ammonium bases.

The invention also relates to a process for the preparation of the compound of the formula I and/or a physiologically tolerable salt of the compound of the formula I and/or an optionally stereoisomeric form of the compound of the formula I, which comprises A) treating an appropriately substituted 5-methylisoxazole-3-carboxamide or -anilide at low temperature, possibly at –80 to –40° C., with an excess (about 3 equivalents) of strong organic or preferably organometallic bases such as butyllithium, tert-butyllithium or lithium diisopropylamide in anhydrous organic solvents, such as diethyl ether, tetrahydrofuran or tert-butyl methyl ether, a deprotonation of the methyl group taking place in addition to the base-induced ring opening and this deprotonated intermediate leading with electrophilic reagents such as aldehydes, ketones or carbon dioxide, after appropriate working up by acidification and extraction, to an addition to the carbonyl group in the sense of a C—C linkage or B) converting a carboxylic acid which can be substituted by further functional groups, or groups present in the form of protected precursors, into an acid halide, preferably an acid chloride, by processes known from the literature, and reacting with the deprotonated form of a suitably substituted cyanoacetamide or -anilide in the sense of a condensation.

The deprotonation of the cyanoacetic acid derivative is preferably carried out by means of sodium hydride in an aprotic anhydrous solvent such as tetrahydrofuran or dichloromethane. Deprotonation and condensation preferably proceed in a temperature range from 0° C. to room temperature. The protective groups optionally additionally carried for the protection of further functional groups are then removed by processes known from the literautre. Process B) is particularly suitable for the preparation of chiral compounds whose centers of asymmetry in the carboxylic acid moiety can additionally be carried with defined chirality, as explained by way of example in Example 10, in the form of a protected secondary or tertiary alcohol, while according to process A)

the chiral secondary alcohols as a rule result as enantiomer mixtures. The physiologically tolerable alkali metal, alkaline earth metal and organic ammonium salts, which are usually water-soluble and therefore particularly suitable for intravenous administration, are prepared by dissolving or suspending the parent compound in a protic or polar aprotic solvent and adding the base in equimolar amount or in excess, when using polar aprotic solvents such as water or lower alcohols a clear solution of the corresponding salt usually resulting which can be brought into a solid, preferably crystalline form by freeze-drying, concentration of the solution or precipitation by addition of a nonpolar solvent.

The invention also relates to pharmaceuticals which contain an efficacious amount of at least one compound of the formula I

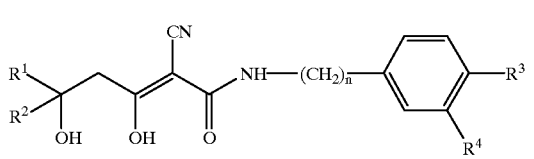
(I)

and/or a physiologically tolerable salt of the compound of the formula I and/or an optionally stereoisomeric form of the compound of the formula I, the radicals $R^1$, $R^2$, $R^3$ and $R^4$ being defined as above, together with a pharmaceutically suitable and physiologically tolerable excipient or carrier, additive and/or other active compounds and auxiliaries.

On account of the pharmacological properties, the compounds according to the invention are outstandingly suitable for the prophylaxis and therapy of all those diseases or disorders whose course involves increased connective tissue and cartilage degradation. These are especially diseases of the locomotory apparatus such as inflammatorily, immunologically or metabolically related acute and chronic arthritides and arthropathies, but also myalgies, disorders of the bone metabolism, as well as degenerative joint diseases. Included among these are osteoarthroses and spondyloses, but also chondrolysis after joint trauma or relatively long immobilization.

The invention furthermore relates to the use of the compound of the formula I for the production of pharmaceuticals for the prophylaxis and therapy of diseases of the connective tissue such as collagenoses and peridontal tissue changes.

The invention also relates to a process for the production of a pharmaceutical, which comprises bringing at least one compound of the formula I into a suitable administration form with a pharmaceutically suitable and physiologically tolerable excipient and, if appropriate, further suitable active compounds, additives and auxiliaries.

Suitable solid or pharmaceutical preparation forms are, for example, granules, powders, coated tablets, tablets, (micro)capsules, suppositories, syrups, juices, suspensions, emulsions, drops or injectable solutions and also preparations with sustained release of active compound, in whose preparation customary auxiliaries, such as excipients, disintegrants, binders, coating agents, swelling agents, glidants or lubricants; flavorings, sweeteners and solubilizers are used. Frequently used auxiliaries which may be mentioned are magnesium carbonate, titanium dioxide, lactose, mannito I and other sugars, talc, lactoprotein, gelatin, starch, cellulose and its derivatives, animal and vegetable oils such as cod-liver oil, sunflower oil, groundnut oil or sesame oil, polyethylene glycol and solvents such as, for example, sterile water and mono- or polyhydric alcohols such as glycerol.

The pharmaceutical preparations are preferably prepared and administered in dose units, each unit containing as active constituent a specific dose of the compound of the formula I according to the invention. In a case of solid dose units such as tablets, capsules, coated tablets or suppositories, this dose can be up to approximately 1000 mg, but preferably from approximately 50 to 300 mg and in the case of injection solutions in ampoule form up to approximately 300 mg, but preferably from approximately 10 to 100 mg.

For the treatment of an adult patient of weight approximately 70 kg, depending on the efficacy of the compounds according to formula I, daily doses of approximately 20 mg to 1000 mg of active compound, preferably from 100 mg to 500 mg, are indicated. Under certain circumstances, however, even higher or lower daily doses may be appropriate. The daily dose can be administered both by single administration in the form of an individual dose unit or else of several smaller dose units and also by repeated administration of subdivided doses at specific intervals.

EXAMPLE 1

N-(Phenyl)-2-cyano-3,5-dihydroxy-5-methylhex-2-enecarboxamide 0.025 mol (5 g) of 4-phenylaminocarbonyl-5-methylisoxazole is dissolved in 320 ml of anhydrous tetrahydrofuran under protective gas (argon). 0.08 mol (32 ml, of butyllithium (2.5 molar in hexane) is then added dropwise in a cooling bath (−78° C.), a temperature rise to −55° C. being observed. After stirring at −78° C. for one hour, 0.13 mol (7.4 g) of absolute acetone is then added dropwise and, after a further 1 ½ hours at −78° C., the mixture is hydrolyzed with 20 ml of water and warmed to approximately 0° C. A pH of 2 is established using 1N hydrochloric acid, the mixture is extracted with ethyl acetate, the organic phase is washed twice with water and once with saturated NaCl solution, then dried using $Na_2SO_4$ and concentrated under reduced pressure, and the residue is crystallized from ethyl acetate and petroleum ether. The colorless crystals obtained have a melting point of 103° C.

Yield: 3.8 g (58%)

EXAMPLE 10a

N-(4-Trifluoromethylphenyl)-2-cyano-3,5-dihydroxyhex-2-enecarboxamide Lysinium Salt, R Isomer Stage 1:
Ethyl (R)-(−)-3-triisopropylsilyloxybutyrate
0.077 mol (10.0 g) of ethyl(R)-3-hydroxybutyrate is dissolved in 90 ml of dimethylformamide and 0.151 mol (10.3 g) of imidazole is added. The mixture is cooled to 0° C. under protective gas in an ice bath and 0.083 mol (16.05 g) of triisopropylsilyl chloride is added dropwise over 5 min. The mixture is stirred at room temperature for a further 5 hours, hydrolyzed with water, the product is extracted with tert-butyl methyl ether, and the organic phase is dried using $Na_2SO_4$ and concentrated under reduced pressure on a rotary evaporator.

Yield: 21.78 g (99.8%) of a highly liquid oil.

Stage 2:
(R)-3-Triisopropylsilyloxybutyric Acid
0.0755 mol (21.78 g) of the product from stage 1 is stirred at 60° C. for 5 days in 1.51 liters of a 0.01 molar lithium hydroxide solution in a tetrahydrofuran/water 1:1 mixture. The mixture is acidified with aqueous citric acid and the product is extracted with ethyl acetate. The organic phase is washed with water, dried over sodium sulfate and concentrated under reduced pressure.

Yield: 12.35 g (63%) of an oily product.

Stage 3:
(R)-3-Triisopropylsilyloxybutyryl Chloride 0.0475 mol (12.36 g) of the product from stage 2 is dissolved in 200 ml of absolute dichloromethane and treated with stirring with 0.0523 mol (6.64 g) of oxalyl chloride. After 5 hours at room temperature, the mixture is concentrated under reduced pressure.

Yield: 12.9 g(98%) of an oily product.

Stage 4:
N-(4-Trifluoromethylphenyl)-2-cyano-3-hydroxy-5-(R)-triisopropylsilyloxy-hex-2-enecarboxamide 0.0140 mol (3.2 g) of cyanoacetic acid 4-trifluoromethylanilide is dissolved in 125 ml of anhydrous tetrahydrofuran and cooled to 2 to 5° C. 0.031 mol of NaH.(0.93 g, 80% strength in mineral oil) is added with stirring and under protective gas to the solution, the temperature being kept below 10° C. The mixture is then stirred at room temperature for 2 hours (slight evolution of gas during the course of this). Following this, it is cooled to 10° C. and 0.168 mol (4.69 g) of the product from stage 3 is added in portions. The mixture is additionally stirred at 15° C. for 20 min and 3.2 ml of glacial acetic acid are then added, and the mixture is stirred at 15° C. for a further 30 min, treated with 125 ml of ice water which contains 3.2 ml of concentrated hydrochloric acid and extracted with dichloromethane. The organic phase is washed with water and saturated sodium chloride solution, dried using sodium sulfate and concentrated on a rotary evaporator.

Yield: 9.1 g of crude product which is chromatographed on silica gel (ethyl acetate/petroleum ether, gradient: 1/1 to 12/1). The product fractions are concentrated under reduced pressure.

Yield 0.72 g of an oily product.

Stage 5:
N-(4-Trifluoromethylphenyl)-2-yano-3,5-dihydroxyhex-2-enecarboxamide, R-isomer 0.0015 mol (0.72 g) of the product from stage 4 is dissolved in 30 ml of 2N aqueous methanolic hydrochloric acid at room temperature. After 4 days, the mixture is concentrated under reduced pressure on a rotary evaporator. The precipitate which is deposited in the course of this is filtered off with suction and dried.

Yield: 0.36 g; Melting point: 156° C., specific rotation: −18° C.(c=1 in ethanol).

The enantiomer purity determined by HPLC is >98%.

EXAMPLE 10b

N-(4-Trifluormethylphenyl)-2-cyano-3,5-dihydroxyhex-2-enecarboxamide Lysinium Salt, S-isomer Preparation is carried out analogously to Example 10a starting from ethyl (S)-3-hydroxybutyrate melting point: 157° C., specific rotation:+16.9°(c=1 in ethanol).

The enantiomer purity determined by HPLC is >98%.

EXAMPLE 37

N-(4-Trifluoromethylphenyl)-2-cyano-3,5-dihydroxyhex-2-carboxamide Lysinium Salt 0.063 mol (20.0 g) of the product from Example 9 is suspended in 1 liter of water and dissolved by addition of 0.063 mol (10.3 g) of lysine×H$_2$O at a pH of 7.2 . The solution is filtered and freezedried. The largely amorphous substance has a melting point of 135–138° C.

Yield: 27.74 g (96%).

Examples 38 and 39 are Prepared Analogously to Example 37

PHARMACOLOGICAL EXAMPLES

Cartilage cells can maintain their characteristic cartilage matrix metabolism ex vivo in suitable cell or tissue culture, i.e. the controlled synthesis and degradation of the matrix macromolecules, over a period of several weeks to months. These processes can be chemically influenced. In the following experimental descriptions, on the one hand, the action of test compounds on the normal renewal of the cartilage matrix proteoglycans by the chondrocytes is described (A), and on the other hand the action on a pathologically increased proteoglycan degradation and also inhibited synthesis in chondrocytes or cartilage tissue by addition of interleukin-1 (B). In both assays, the stimulating action of the test substance is expressed by a stimulation factor which is calculated from the quotient of the specific proteoglycan content under the active compound condition divided by the proteoglycan content under the control condition. In Experiment A, the control condition is the untreated control group and in experimental procedure B this is the interleukin-1 (IL-1)-treated control group. A factor=1 can thus identify no action, a factor of >1 points to a stimulation and a factor of <1 to an inhibitory action.

A) Modulation of the chondrocytic proteoglycan metabolism (PG stimulation)

Cartilage samples are taken under sterile conditions from fetlock joints of freshly slaughtered bulls, incubated with 1% strength pronase (Boehringer) solution in Ham's F12 medium (Serva) at 37° C. for 1 hour, and the enzyme solution is replaced by a 0.025% strength collagenase type A (Worthington) solution in medium and incubated overnight. After filtering through a 50 μm nylon filter, centrifugation, resuspension and vitality testing, a cell suspension of 4×10$^6$ cells/ml of medium, enriched with 20% fetal calf serum, is prepared and mixed at approximately 38° C. with 2% strength low-melting agarose (Seplaque) in the ratio 1:1 and 0.1 ml of this is pipetted into each well of a 24 well microtiter plate. After gelling, the samples are covered with a layer of 0.5 ml/well of medium, which is enriched with 5% serum, 25 μm/ml of ascorbic acid, and in groups of up to 6–8 wells with 10 μm of the test substance. The medium in a constant composition is renewed every second day for a treatment period of 8 days. At the end of the treatment, washing is carried out with medium, 1 ml of a buffered (pH 5.6) 1% strength Alcian Blue (Sigma) solution, enriched with 25% strength glutaraldehyde in the ratio 7:1, per well is added and the mixture is incubated for 48 hours. After washing and differentiating with 3% strength acetic acid, dehydration is carried out up to 70% strength ethanol content by means of the rising alcohol series, and then the bound dye is extracted at 4° C. for 24 hours using 8 M guanidine hydrochloride. The stoichiometric binding of the Alcian Blue to the chondroitin sulfate side chains of the proteoglycans allows a quantification of the enriched matrix via the determination of the extinction of the dye solution at 610 nm. Table 1 shows the results.

B) Modulation of the IL-1-induced Chondrocytic Chondrolysis (Chondrolysis Compensation)

Cell preparation was carried out as described under A), if cartilage tissue explants are used these are added directly to the enriched culture medium described above after stamping out cartilage disks of 4 mm diameter and a depth which includes the entire cartilage layer. After adaptation for 5 days, interleukin-1 is added to the medium, 8 units/well for the cell culture, 20 units/well for the tissue culture, and, over the treatment period of 8 days, likewise added again every second day on changing the medium. At the end of the experiments, 1 μCi of $Na_2^{35}SO_4$/well is added and the mixture is incubated for 24 hours. After removing the supernatant, the remaining gels or explants are broken down in the microtiter plates by repeated deepfreezing and thawing and extracted with 8 M guanidine hydrochloride. After centrifugation, the supernatant is separated on a PD10 Sephadex column into free and incorporated sulfate and the radioactivity of the samples, which is a measure of the amount of proteoglycan newly formed, is determined in a β counter. Table 1 shows the results.

Note to Table 1:

Examples 2–9 and 11–33 were prepared analogously to Example 1 using the appropriately substituted (commercially available) aldehydes or ketones as electrophilic reagents. To prepare Examples 34 and 35, 3-methyl-(5-oxohexyl)-7-propylxanthine (propentofylline) and 1-(5-oxohexyl)theobromine (pentoxifylline) were employed. Example 36 was synthesized by use of solid $CO_2$ as an electrophile.

$^1$H-NMR spectra have been recorded on a 200 MHz apparatus from Varian, as a rule using tetramethylsilane (TMS) as the internal standard and at room temperature 22–26° C. (RT). Temperature details in degrees Celsius. The abbreviations used are either explained or correspond to the customary conventions.

TABLE 1

| Ex. | Structure | Solvent ¹H-NMR | M.p. (° C.) | PG stimulation | Chondrolysis compensation |
|---|---|---|---|---|---|
| 1 | ![structure with NH-phenyl] | DMSO 1.26 (s,6H) 2.69 (s,2H) 7.15 (m,1H) 7.36 (m,2H) 7.55 (m,2H) 9.25 (b,2H) 10.25 (s,1H) | 103 | | 1.4 |
| 2 | ![structure with NH-phenyl-CF3] | DMSO 1.25 (s,6H) 2.69 (s,3H) 7.68 and 7.81 (in each case m,2H) 9.2 (b,1H) 10.7 (s,1H) | 155 | 1.8 | 1.9 |
| 3 | ![structure with NH-CH2-phenyl] | DMSO 1.09 (s,6H) 2.42 (s,2H) 4.30 (d,2H) 7.25 (m,5H) 9.75(m,1H) | >190 amorphous | | 1.5 |
| 4 | ![structure with NH-CH2CH2-phenyl] | DMSO 1.23 (s,6H) 2.61 (s,2H) 2.80 (m,2H) 3.40 (m,2H) 7.26 (m,5H) 8.50 (b,1H) | 81 | | 1.5 |

TABLE 1-continued

| Ex. | Structure | Solvent ¹H-NMR | M.p. (° C.) | PG stimulation | Chondrolysis compensation |
|---|---|---|---|---|---|
| 5 | (structure) | DMSO 1.17 (d,3H) 2.65 (m,2H) 4.08 (m,1H) 7.15 (m,1H) 7.35 (m,2H) 7.54 (m,2H) 8.75 (b,2H) 10.25 (s,1H) | 101 | | 1.8 |
| 6 | (structure) | DMSO 1.05 (d,3H) 2.55 (m,2H) 4.00 (m,1H) 4.20 (m,2H) 4.80 (b,1 H) 7.25 (m,5H) 8.45 (b,2H) 9.75 (b,1H) | >157 amorphous | | 1.9 |
| 7 | (structure) | DMSO 1.13 (d,3H) 2.55 (m,2H) 2.80 (m,1H) 7.25 (m,5H) 8.45 (b,2H) 16.5 (b,1H) 4.03 (m,1H) | 91 | | 1.3 |
| 8 | (structure) | DMSO 1.16 (d,3H) 2.63 (m,2H) 4.05 (m,1H) 7.39 and 7.57 (in each case m,2H) 9.60 (b,2H) 10.25(s,1H) | 152 | | 2.1 |

TABLE 1-continued

| Ex. | Structure | Solvent | ¹H-NMR | M.p. (° C.) | PG stimulation | Chondrolysis compensation |
|---|---|---|---|---|---|---|
| 9 | (structure) | DMSO | 1.07 (m,3H) 2.50 (m,2H) 4.04 (m,1H) 7.10 (b,1H) 7.54 and 7.70 (in each case m,2H) 12.45 (s,1H) | 160 Razemat | 1.5 | 1.6 |
| 10a | (structure) | DMSO | 1.07 (m,3H) 2.50 (m,2H) 4.04 (m,1H) 7.10 (b,1H) 7.54 and 7.70 (in each case m,2H) 12.45 (s,1H) | 156 | | 1.1 |
| 10b | (structure) | DMSO | 1.07 (m,3H) 2.50 (m,2H) 4.04 (m,1H) 7.10 (b,1H) 7.54 and 7.70 (in each case m,2H) 12.45 (s,1H) | 157 | | 1.7 |
| 11 | (structure) | DMSO | 2.90 (m,2H) 5.05 (m,1H) 7.35 (m,5H) 7.65 and 7.75 (in each case m,2H) 9.10 (m,2H) 10.95 (s,1H) | 170–171 | | |

TABLE 1-continued

| Ex. | Structure | Solvent | ¹H-NMR | M.p. (° C.) | PG stimulation | Chondrolysis compensation |
|---|---|---|---|---|---|---|
| 12 | (4-Cl-phenyl) | DMSO | 2.85 (m,2H) 5.05 (m,1H) 6.80 (b,2H) 7.39 (m,7H) 7.59 (m,2H) 10.85 (s,1H) | 178 | | |
| 13 | (3-methyl-4-Cl-phenyl) | DMSO | 2.32 (s,3H) 288 (m,2H) 5.03 (m,1H) 7.35 (m,8H) 9.60 (b,2H) 10.40 (s,1H) | 165 | | 1.1 |
| 14 | (4-CF₃-phenyl, 4-methylphenyl) | DMSO | 2.29 (s,3H) 2.82 (m,2H) 5.00 (m,1H) 7.15 and 7.26 (in each case m,2H) 7.72 (m,6H) 11.05 (s,1H) | 180 | | |
| 15 | (4-CF₃-phenyl, 4-benzyloxyphenyl) | DMSO | 2.80 (m,2H) 5.00 (m,1H) 5.09 (s,2H) 7.00 (m,2H) 7.35 (m,7H) 7.71(m,6H) 11.12 (s,1H) | from 200 | | 1.2 |

TABLE 1-continued

| Ex. | Structure | Solvent ¹H-NMR | M.p. (° C.) | PG stimulation | Chondrolysis compensation |
|---|---|---|---|---|---|
| 16 | 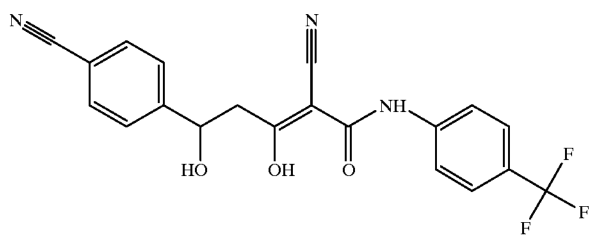 | DMSO 2.82 (m,2H) 5.12 (m,1H) 7.62 (m,4H) 7.90 (m,6H) 11.40 (s,1H) | 180 | | 1.1 |
| 17 | 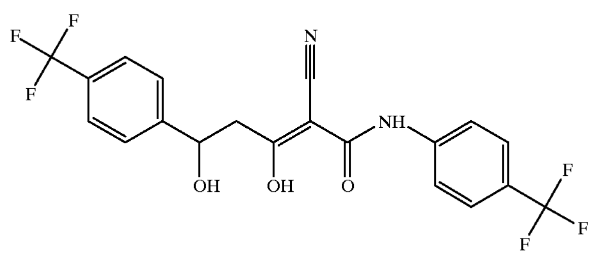 | DMSO 2.85 (m,2H) 5.15 (m,1H) 7.20 (b,2H) 7.70 (m,8H) 11.40 (s,1H) | 178 | | |
| 18 | 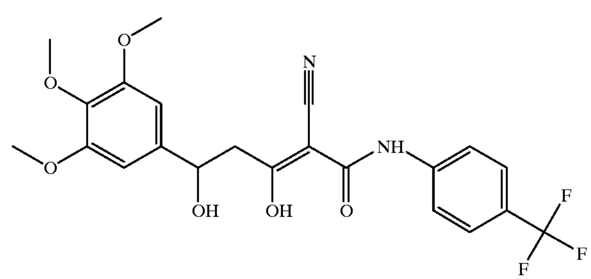 | DMSO 2.89 (m,2H) 3.64 (s,3H) 3.78 (s,6H) 4.90 (m,1H) 6.70 (s,2H) 7.67 and 7.74 (in each case m,2H) 9.60 (b,2H) | 154 | 1.1 | 1.2 |

TABLE 1-continued

| Ex. | Structure | Solvent | ¹H-NMR | M.p. (° C.) | PG stimulation | Chondrolysis compensation |
|---|---|---|---|---|---|---|
| 19 | (structure) | DMSO | 2.79 (m,2H) 4.95 (m,1H) 5.99 (s,2H) 6.89 (m,3H) 7.65 and 7.77 (in each case m,2H) 8.85 (b,2H) 11.15 (s,1H) | 228 amorphous | 1.1 | 1.3 |
| 20 | (structure) | DMSO | 2.83 (m,2H) 5.25 (m,1H) 7.56 and 7.70 in each case m,2H) 7.90 and 8.78 (in each case M,2H) 12.35 (s,1H) | 203 | | |
| 21 | (structure) | DMSO | 2.92 (m,2H) 5.31 (m,1H) 7.57 and 7.71 (in each case m,2H) 8.05 (m,1H) 8.55 (m,1H) 8.80 (m,1H) 8.90 (b,2H) 12.25 (s,1H) | 203 | 1.2 | 1.3 |
| 22 | (structure) | DMSO | 2.91 (m,2H) 5.02 (m,1H) 5.95 (b,2H) 6.30 (m,1H) 6.38 (m,1H) 7.58 (m,1H) 7.59 and 7.74 (in each case m,2H) 11.65 (s,1H) | from 180 | 1.1 | 1.9 |

TABLE 1-continued

| Ex. | Structure | Solvent | ¹H-NMR | M.p. (° C.) | PG stimulation | Chondrolysis compensation |
|---|---|---|---|---|---|---|
| 23 | (4-trifluoromethylphenyl)amide of 2-cyano-3-hydroxy-5-(furan-3-yl)-5-hydroxy-pent-2-enoic acid | DMSO | 2.85 (m,2H) 4.97 (m,1H) 6.47 (m,1H) 6.56 (m,2H) 7.63 (m,6H) 11.40 (s,1H) | 146 | | 1.9 |
| 24 | (4-trifluoromethylphenyl)amide of 2-cyano-3-hydroxy-5-(thiophen-2-yl)-5-hydroxy-pent-2-enoic acid | DMSO | 2.98 (m,2H) 5.30 (m,1H) 7.00 (m,1H) 7.25 (b,2H) 7.45 (m,2H) 7.67 and 7.79 (in each case m,2H) 11.10 (s,1H) | >200 stable | | 1.9 |
| 25 | (4-trifluoromethylphenyl)amide of 2-cyano-3-hydroxy-5-hydroxy-7-phenyl-hepta-2,6-dienoic acid | DMSO | 2.77 (m,2H) 4.60 (m,1H) 6.35 (m,1H) 6.65 (m,1H) 7.30 (m,5H) 7.65 and 7.78 | 168–172 | | |
| 26 | (4-trifluoromethylphenyl)amide of 2-cyano-3-hydroxy-5-hydroxy-7-phenyl-hept-2-en-6-ynoic acid | DMSO | 2.95(m,2H) 4.88 (m,1H) 5.55 (b,2H) 7.40 (m,5H) 7.63 and 7.77 (in each case m,2H) 11.60 (s,1H) | 168 | | 1.9 |

TABLE 1-continued

| Ex. | Structure | Solvent | $^1$H-NMR | M.p. (°C.) | PG stimulation | Chondrolysis compensation |
|---|---|---|---|---|---|---|
| 27 | 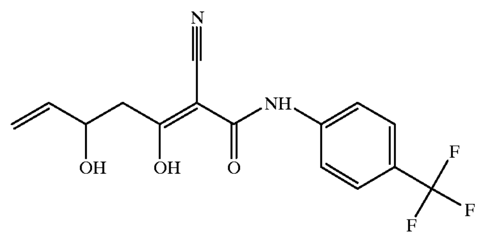 | DMSO | 2.69 (m,2H) 4.45 (m,1H) 5.18 (m,2H) 5.92 (m,1H) 7.67 and 7.80 (in each case m,2H) 9.15 (b,2H) 11.0 (s,1H) | 141 | 1.7 | 1.6 |
| 28 | 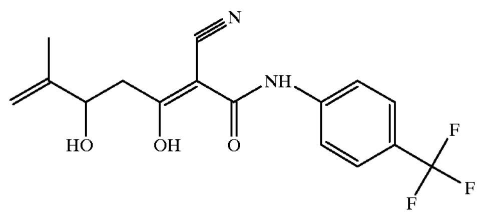 | DMSO | 1.72 (s,3H) 2.70 (m,2H) 4.34 (m,1H) 4.87 (m,2H) 7.65 and 7.77 (in each case m,2H) 11.18 (s,1H) | 162 stable | 1.1 | |
| 29 | 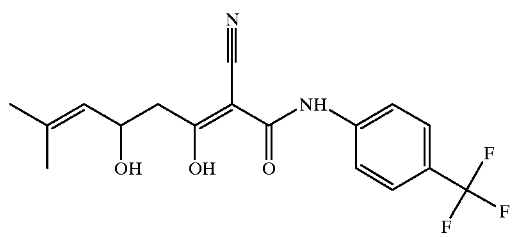 | DMSO | 1.65 (m,6H) 2.62 (m,2H) 4.65 (m,1H) 5.19 (m,1H) 6.45 (b,3H) 7.73 and 7.78 (in each case m,2H) | 155 stable | 1.1 | 1.7 |
| 30 | 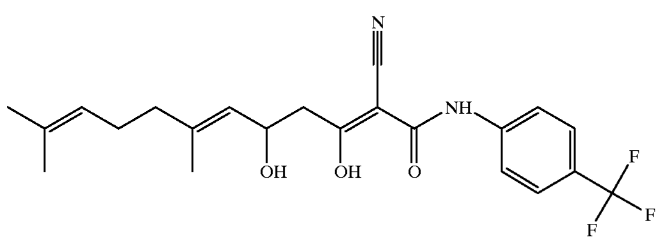 | DMSO | 1.55 (m,3H) 1.62 (m,6H) 2.00 (m,4H) 2.60 (m,2H) 4.65 (m,1H) 5.05 (m,1H) | 114–116 stable | | 1.3 |

TABLE 1-continued

| Ex. | Structure | Solvent | ¹H-NMR | M.p. (° C.) | PG stimulation | Chondrolysis compensation |
|---|---|---|---|---|---|---|
| 31 | 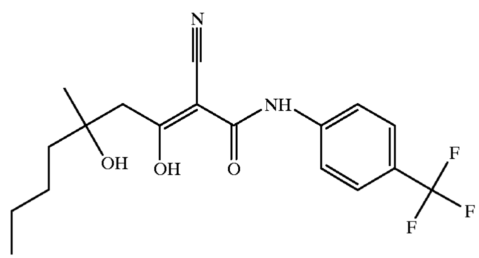 | DMSO | 0.88 (t,3H) 1.16 (s,3H) 1.30 (m,6H) 2.60 (s,2H) 6.80 (b,2H) 7.64 and 7.77 (in each case m,2H) 11.30 (s,1H) | 157 stable | | 1.6 |
| 32 | 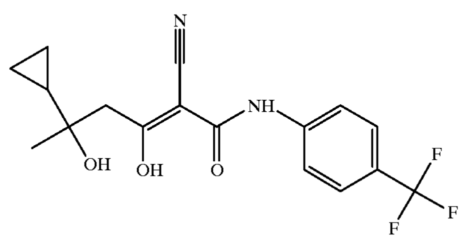 | DMSO | 0.30 (m,4H) 0.95 (m,1H) 1.21 (s,3H) 2.70 (s,2H) 5.15 (b,2H) 7.66 and 7.79 (in each case m,2H) 11.10 (s,1H) | 162 stable | 1.1 | 1.8 |
| 33 | 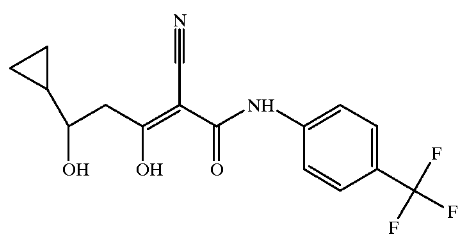 | DMSO | 0.30 (m,4H) 0.90 (m,1H) 2.74 (m,2H) 3.34 (m,1H) 7.35 (b,2H) 7.66 and 7.68 (in each case m,2H) 10.83 (s,1H) | 169 stable | | 1.9 |
| 34 | 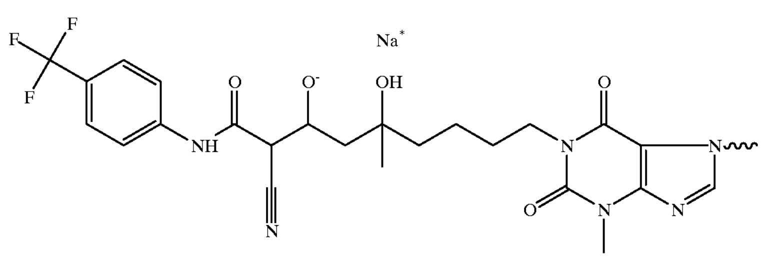 | DMSO | 0.82 (t,3H) 1.16 (s,3H) 1.45 (m,6H) 1.75 (q,2H) 2.60 (s,2H) 3.42 (s,3H) 3.85 (m,3H) 4.20 (t,2H) 5.80 (b,2H) 7.64 and 7.78 (in each case m,2H) 8.08 (s,1H) 11.25 (s,1H) | 170–175 | | |

TABLE 1-continued

| Ex. | Structure | Solvent | ¹H-NMR | M.p. (° C.) | PG stimulation | Chondrolysis compensation |
|---|---|---|---|---|---|---|
| 35 | 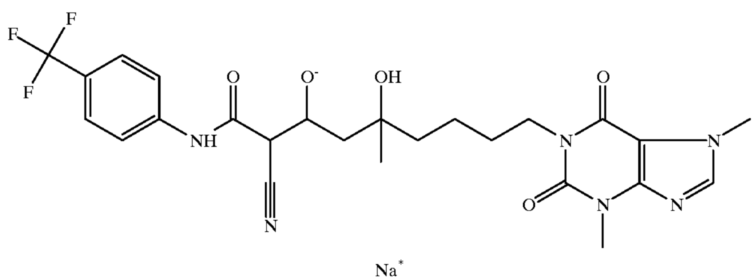 | DMSO | 1.11 (s,3H) 1.45 (m,6H) 2.60 (s,2H) 3.36 (b,2H) 3.42 (s,3H) 3.85 (m,2H) 5.80 (b,2H) 7.56 and 7.74 (in each case m,2H) 8.01 (s,1H) 12.30 (s,1H) | 175–180 amorphous | 1.1 | |
| 36 | 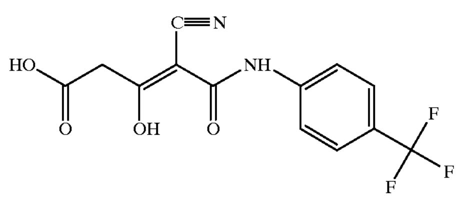 | DMSO | 3.41 (s,2H) 7.59 and 7.73 (in each case m,2H) 9.10 (b,2H) 11.75(s,1H) | from 200 amorphous | | 1.8 |
| 37 | 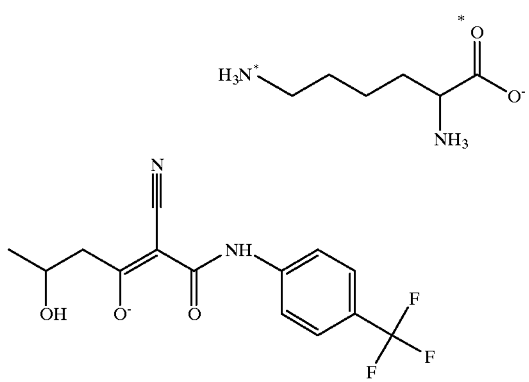 | DMSO | 1.09 (d,3H) 1.55 (m,6H) 2.50 (m,2H) 2.78 (m,2H) 3.22 (m,1H) 4.03 (m,1H) 7.55 and 7.71 (in each case m,2H) 7.80 (b,7H) 12.46 (s,1H) | 135–138 amorphous | 1.1 | 1.9 |

TABLE 1-continued

| Ex. | Structure | Solvent | ¹H-NMR | M.p. (° C.) | PG stimulation | Chondrolysis compensation |
|---|---|---|---|---|---|---|
| 38 | (structure) | DMSO | 1.17 (s,6H) 1.55 (m,6H) 2.50 (m,2H) 2.78 (m,2H) 3.28 (m,1H) 7.56 and 7.74 (in each case m,2H) 7.90 (b,7H) 12.31 (s,1H) | 145–148 amorphous | | 1.8 |
| 39 | (structure) | DMSO | 1.55 (m,6H) 2.50 (m,2H) 2.78 (m,2H) 3.45 (m,1H) 5.10 (m,2H) 5.95 (m,1H) 7.55 and 7.72 (in each case m,2H) 7.80 (b,7H) 12.45 (s,1H) | 133–135 amorphous | 1.7 | 1.6 |

What is claimed is:

1. A compound of the formula I

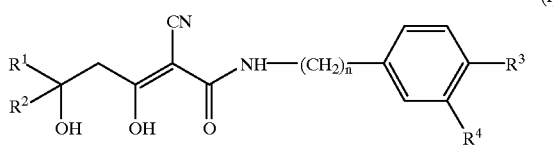

in any stereoisomeric form, or a salt thereof,
wherein
$R^1$ is a hydrogen atom or $(C_1-C_4)$-alkyl,
$R^2$ is pyridyl,
$R^3$ is
  a) —$CF_3$,
  b) —O—$CF_3$,
  c) —S—$CF_3$,
  d) —OH,
  e) —$NO_2$,
  f) halogen,
  g) benzyl,
  h) phenyl,
  i) —O-phenyl,
  j) a hydrogen atom,
  k) —CN, or
  l) —C-phenyl, mono- or polysubstituted by
    1) $(C_1-C_4)$-alkyl,
    2) halogen,
    3) —O—$CF_3$ or
    4) —O—$CH_3$,
$R^4$ is
  a) $(C_1-C_4)$-alkyl,
  b) halogen, or
  c) a hydrogen atom, and
n is the integer zero, 1, 2, 3 or 4.

2. A compound as claimed in claim 1, wherein
$R^1$ is a hydrogen atom or methyl,
$R^3$ is
  a) —$CF_3$,
  b) —Cl or
  c) a hydrogen atom,
$R^4$ is
  a) a hydrogen atom or
  b) methyl, and
n is the integer zero, 1 or 2.

3. A process for the preparation of a compound as claimed in claim 1, which comprises
  A) treating an appropriately substituted 5-methylisoxazole-3-carboxamide or -anilide, at a low temperature, with an excess of about 3 equivalents of a strong organic or organometallic base in an anhydrous organic solvent, to deprotonate the methyl group and induce the ring-opening, treating this deprotonated intermediate with an electrophilic reagent, and working up by acidification and extraction, to result in the addition to the carbonyl group in the sense of a C—C linkage, or
  B) converting a carboxylic acid which can be substituted by further functional groups, or groups present in the form of protected precursors, into an acid halide, and reacting the acid halid with a deprotonated form of a suitably substituted yanoacetamide or -anilide in the sense of a condensation.

4. A process as claimed in claim 3, wherein in A) the low temperature is −80 to −40° C.

5. A process as claimed in claim 3, wherein in A) the base is an organometallic base selected from the group consisting of butyllithium, tert-butyllithium and lithium diisopropylamide.

6. A process as claimed in claim 3, wherein in A) the anhydrous organic solvent is selected from the group consisting of diethyl ether, tetrahydrofuran and tert-butyl methyl ether.

7. A process as claimed in claim 3, wherein in A) the electrophilic reagent is selected from the group consisting of an aldehyde, a ketone and carbon dioxide.

8. A process as claimed in claim 3, wherein in B) the acid halide is an acid chloride.

9. A pharmaceutical composition comprising a pharmaceutically effective amount of at least one compound as claimed in claim 1, together with a pharmaceutically suitable and physiologically tolerable carrier.

10. A method for the therapy of a disease or disorder characterized by increased connective tissue or cartilage degradation, which comprises administering to a host in need of such therapy a pharmaceutical composition as claimed in claim 9.

11. A method for the therapy of a disease or disorder characterized by increased connective tissue or cartilage degradation, which comprises administering to a host in need of such therapy an effective amount of at least one compound as claimed in claim 1.

12. A method as claimed in claim 11, wherein a disease of the locomotory apparatus, a myalgia, a disorder of the bone metabolism, or a degenerative joint disease is treated.

13. A method as claimed in claim 12, wherein the disease of the locomotory apparatus is inflammatorily, immunologically or metabolically related acute or chronic arthritides or arthropathies.

14. A method as claimed in claim 12, wherein the degenerative joint disease is osteoarthroses, spondyloses, or chrodrolysis after joint trauma or immobilization.

15. A method as claimed in claim 10, wherein a disease of the locomotory apparatus, a myalgia, a disorder of the bone metabolism, or a degenerative joint disease is treated.

16. A method as claimed in claim 15, wherein the disease of the locomotory apparatus is inflammatorily, immunologically or metabolically related acute or chronic arthritides or arthropathies.

17. A method as claimed in claim 15, wherein the degenerative joint disease is osteoarthroses, spondyloses, or chrodrolysis after joint trauma or immobilization.

18. A method as claimed in claim 10, wherein the disease is selected from the group consisting of collagenoses and peridontal tissue changes.

19. A method as claimed in claim 11, wherein the disease is selected from the group consisting of collagenoses and peridontal tissue changes.

* * * * *

UNITED STATES PATENT AND TRADEMARK OFFICE
CERTIFICATE OF CORRECTION

PATENT NO. : 6,387,934 B1  Page 1 of 1
DATED : May 14, 2002
INVENTOR(S) : Wilfried Schwab et al.

It is certified that error appears in the above-identified patent and that said Letters Patent is hereby corrected as shown below:

<u>Column 33,</u>
Line 21, "t) halogen" should read -- f) halogen --.

<u>Column 34,</u>
Line 2, "halid" should read -- halide --.
Line 3, "yanoacetamide" should read -- cyanoacetamide --.

Signed and Sealed this

Twenty-third Day of July, 2002

Attest:

JAMES E. ROGAN
Attesting Officer    Director of the United States Patent and Trademark Office